United States Patent [19]

Mori et al.

[11] Patent Number: 4,604,240
[45] Date of Patent: Aug. 5, 1986

[54] HOMOBRASSINOLIDE, AND ITS PRODUCTION AND USE

[75] Inventors: Kenji Mori, Tokyo; Tetsuo Takematsu, Tochigi; Masayuki Sakakibara, Chiba; Hiromichi Oshio, Osaka, all of Japan

[73] Assignee: Sumitomo Chemical Company, Limited, Osaka, Japan

[21] Appl. No.: 680,471

[22] Filed: Dec. 11, 1984

Related U.S. Application Data

[63] Continuation of Ser. No. 443,018, Nov. 19, 1982, abandoned.

[30] Foreign Application Priority Data

Nov. 24, 1981 [JP] Japan .................................. 56-188818

[51] Int. Cl.[4] .............................................. C07J 71/00
[52] U.S. Cl. .................................... 540/114; 260/397.2
[58] Field of Search ...................... 260/239.55 R, 397.2

[56] References Cited

U.S. PATENT DOCUMENTS 4,346,226  8/1982  Thompson et al. ................. 549/268
4,453,967  6/1984  Mori ................................... 549/268

OTHER PUBLICATIONS

Mori et al., "Tetrahedron", vol. 38 (1982), No. 14, pp. 2099-2109.
J. Chem. Soc. Perkins Trans., vol. 1, (1983), pp. 379-382, article by M. Anastasia et al.

*Primary Examiner*—Elbert L. Roberts
*Attorney, Agent, or Firm*—Birch, Stewart, Kolasch & Birch

[57] ABSTRACT

22R,23R-Homobrassinolide of the formula:

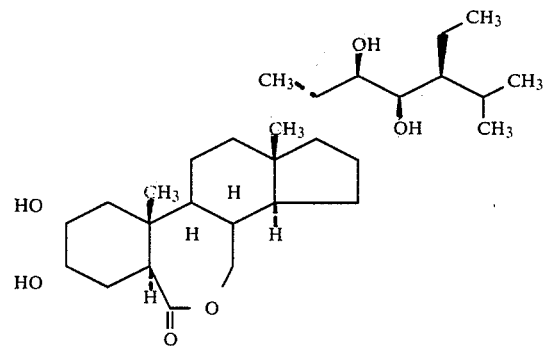

which is useful as a plant growth regulator.

3 Claims, No Drawings

HOMOBRASSINOLIDE, AND ITS PRODUCTION AND USE

This application is a continuation of application Ser. No. 443,018, filed on Nov. 19, 1982 now abandoned.

The present invention relates to homobrassinolide, and its production and use. More particularly, it relates to 2R,3S,22R,23R-tetrahydroxy-24S-ethyl-B-homo-7-oxa-5α-cholestan-6-one (hereinafter referred to as "22R,23R-homobrassinolide") of the formula:

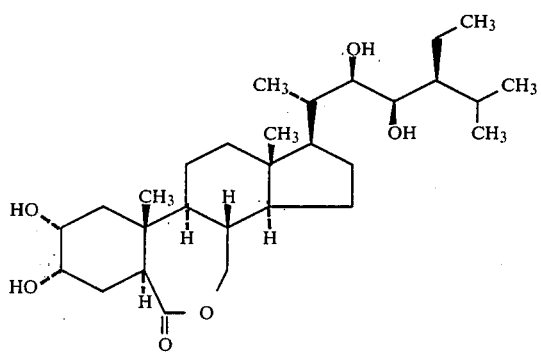

and its production process and its use as a plant growth regulator.

In recent years, a certain steroid named "Brassinolide" having a plant growth promoting activity was isolated from the pollen of Brassica napus L., and a certain chemical structure was assigned thereto [Chem. & Eng. News, No. 5, 20 (1979)]. Subsequently, the synthesis of the structural isomers of the said brassinolide was achieved [J.Org.Chem., 44, 5002 (1979)], but this synthesis requires many and troublesome steps (i.e. 11 steps) starting from ergosterol (i.e. ergosta-5,7,22-trien-3β-ol) and affords the objective structural isomers of brassinolide only in a yield of about 10%. In addition, those steps include the reaction which will take an extremely long time such as two weeks. Further, attempts were made to synthesize brassinolide itself, and some total synthetic methods comprising numerous steps were reported by two research groups [J.Am. Chem. Soc., 102, 6580 (1980); J.Chem.Soc., Chem.Comm., 1980, 962].

Previously, the present inventors succeeded in synthesis of 2R,3S,22S,23S-tetrahydroxy-24S-ethyl-B-homo-7-oxa-5α-cholestan-6-one (hereinafter referred to as "22S,23S-homobrassinolide") having a similar activity to brassinolide from stigmasterol (i.e. stigmasta-5,22-dien-3-ol) [Agr.Biol.Chem., 44, 1211 (1980)]. Homobrassinolide in this report was later proved to be a 22S,23S-isomer by the X ray analysis [Tetrahedron, 38, 2099 (1982)].

As a result of the extensive study, it has now been found that the 22R,23R-homobrassinolide (I) can be efficiently produced from the intermediate in the synthesis of the said 22S,23S-homobrassinolide. The 22R,23R-homobrassinolide (I) is not only different from the 22S,23S-isomer in physico-chemical properties but also exert a remarkably higher plant growth regulating activity than that of the 22S,23S-isomer.

According to the present invention, the 22R,23R-homobrassinolide (I) can be synthesized from stigmasterol substantially as shown in the following scheme:

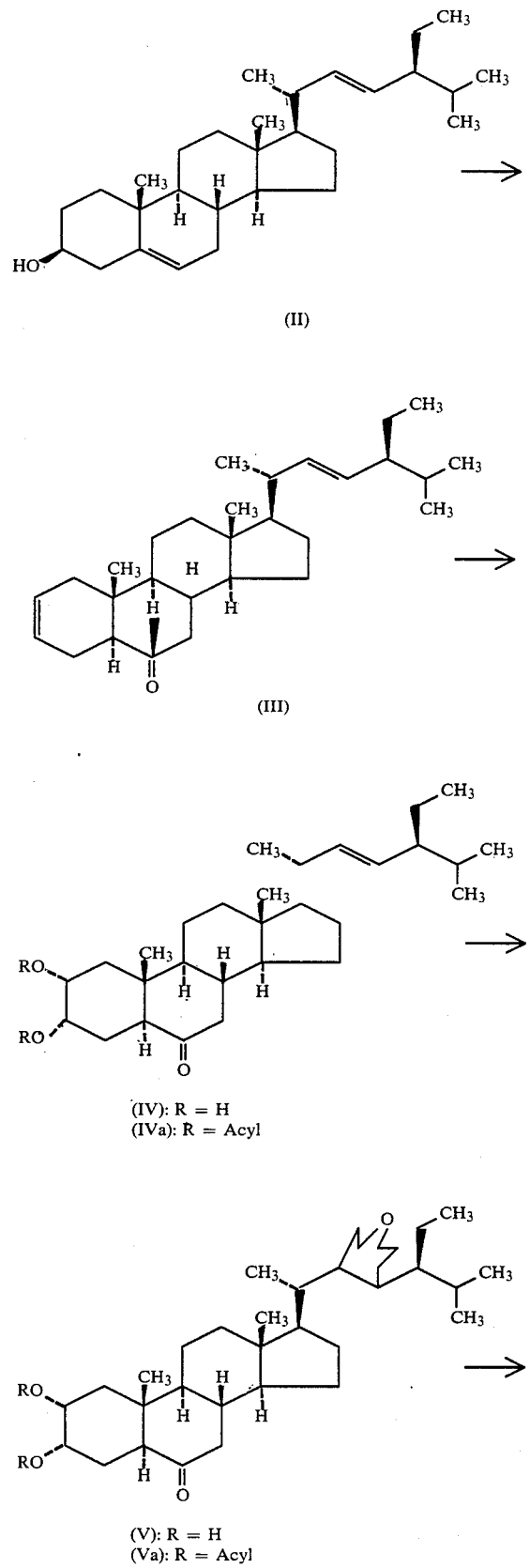

-continued

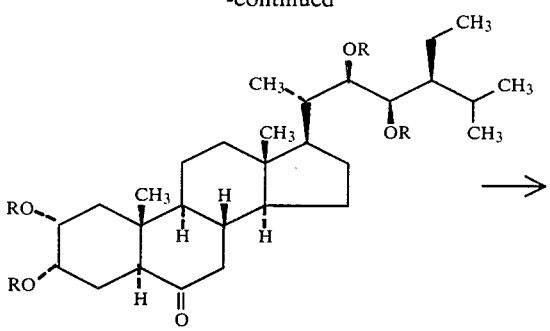

(VI): R = H
(VIa): R = Acyl

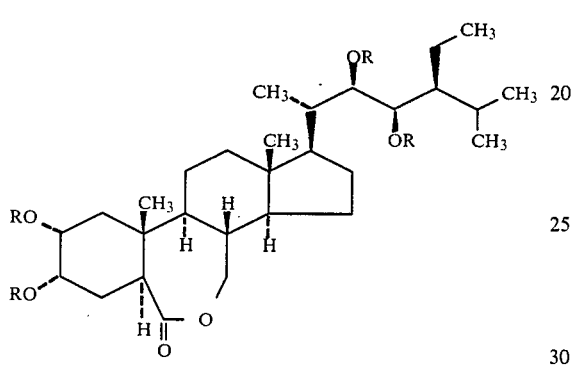

(I): R = H
(Ia): R = Acyl

In the above conversions, the RO group may be hydroxyl or optionally protected hydroxyl, the protective group being a conventional one such as acyl, preferably lower alkanoyl (e.g. acetyl).

The compound (IV) can be produced from stigmasterol according to the known procedure [Summaries of the Speeches at the 1981 Meeting of the Association of Agricultural Chemistry of Japan, page 412].

The compound (IV) is then acylated by a per se conventional procedure, for instance, using acetic anhydride or acetic chloride in the presence of a tertiary amine to give the compound (IVa).

The compound (IVa) is converted into the compound (Va), for instance, by oxidizing the former with an organic peroxide such as an organic peracid (e.g. m-chloroperbenzoic acid). The oxidation is preferably effected in an inert solvent (e.g. dichloromethane) at a temperature of $-10°$ to $80°$ C. for a period of 20 minutes to 24 hours. The amount of the organic peroxide is usually from 1 to 5 mols per 1 mol of the compound (IVa).

Then, the compound (Va) is reacted with hydrobromic acid in acetic acid, followed by treatment with aqueous acetic acid to give the compound (VIa). In the former step, the concentration of hydrobromic acid in acetic acid is not limitative and may be usually about 30%. The amount of hydrobromic acid may be from 5 to 20 times, preferably from 5 to 10 times, of the amount of the compound (Va). The reaction temperature is preferred to be from $0°$ to $100°$ C., particularly from $10°$ to $30°$ C., whereby the proceeding of any side reaction will be suppressed. In the latter step, aqueous acetic acid can serve not only as the reagent but also as the reaction medium and may be employed in an excessive amount such as 5 to 100 times of the amount of the compound (Va). While any limitation is not present on the concentration of acetic acid, it may be usually from 50 to 90%. The reaction temperature and the reaction time are correlated each other but are not limitative. Thus, the reaction may be usually effected at a temperature of $90°$ to $120°$ C. for a period of 3 to 24 hours. When any of the acyl groups is eliminated in the course of the above reaction, the resulting product may be subjected to acylation. The acylation may be accomplished by a per se conventional procedure. Still, the major component in the compound (VIa) is confirmed to be a 22R,23R-isomer by chromatography.

The compound (VIa) is then subjected to oxidative ring expansion to give the compound (Ia). The oxidative ring expansion can be achieved according to the so-called Baeyer-Villiger reaction [e.g. A. Streitwieser, Jr. et al.: "Introduction to Organic Chemistry", Macmillan Publishing Co., Inc., 391 (1976)], for instance, by treatment with an organic peroxide such as trifluoroperacetic acid or m-chloroperbenzoic acid. The use of trifluoroperacetic acid prepared from trifluoroacetic anhydride and hydrogen peroxide as the oxidizing agent is quite advantageous, because the reaction proceeds within a short period of time and affords the compound (Ia) in a high yield and a high purity.

Hydrolysis of the compound (Ia) gives the 22R,23R-homobrassinolide (I). The hydrolysis may be achieved by a per se conventional procedure, e.g. treatment with an alkali metal hydroxide (e.g. potasium hydroxide, sodium hydroxide), followed by treatment with a dilute mineral acid (e.g. dilute hydrochloric acid, dilute sulfuric acid). The treatment is usually made in an inert solvent such as water, an alkanol (e.g. methanol, ethanol), dimethylsulfoxide or a mixture of these solvents.

The products in any of the above steps may be subjected to the next reactions in the crude state. However, the products are preferably purified by a per se conventional refining procedure such as solvent extraction, recrystallization, filtration, column chromatography or thin layer chromatography prior to the use in the subsequent step.

As stated above, the synthesis of the 22R,23R-homobrassinolide (I) can be readily accomplished from easily available stigmasterol in several steps, which do not require any troublesome operation or a long reaction time. Advantageously, the 22R,23R-homobrassinolide (I) is obtainable in a good yield.

Among the products in the above scheme, all the compounds (IVa) to (I) are novel. The tetraacetate of the compound (I) is a 22R,23R-isomer, which is different from the intermediate compound of 22S,23S-isomeric homobrassinolide as shown in Agr.Biol.Chem., 44, 1211 (1980). For instance, the tetraacetate of 22R,23R-isomer (I) is entirely different from the tetraacetate of 22S,23S-isomer of the following formula:

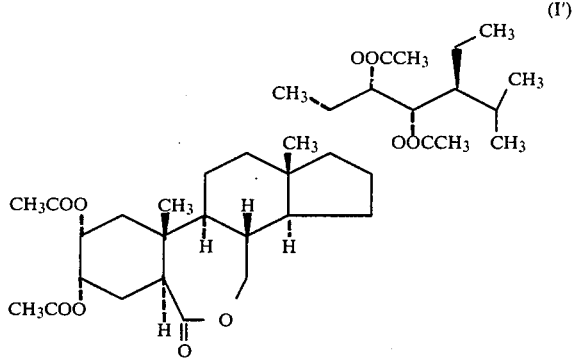

which is an intermediate in the synthesis of 22S,23S-homobrassinolide. Physical properties of the said two different compounds are as follows:

Tetraacetate of Compound (I) (22R,23R-isomer): M.P., 137° to 139° C.; $[\alpha]_D^{24}+36.40°$ (c=0.662, CHCl$_3$).

Compound (I′) (22S,23S-isomer): M.P., 176° to 178° C.; $[\alpha]_D^{20}+24.4°$ (c=1.006, CHCl$_3$).

The 22R,23R-homobrassinolide (I) shows a notable plant growth regulating activity and is useful as a plant growth regulator. For such use, it may be formulated in any preparation form conventionally employed in the agrochemical field. Namely, it may be admixed with solid or liquid carriers or diluents (e.g. mica, talc, clay, diatomeceous earth, water) to make powders, granules, tablets, pellets, solutions, dispersions, suspensions, etc. When desired, auxiliary agents such as emulsifiers may be also incorporated therein.

Application of the said preparation may be effected by a conventional procedure such as spraying, spreading, coating or dipping onto plants (e.g. leaf, stem, fruit, seed) or soils. The amount of the active ingredient to be applied is varied with preparation forms, kinds of plants to be treated, application methods, application times, etc. In general, the concentration of the active ingredient on the application in the form of aqueous solution may be not less than 0.05 ppm, preferably from 0.1 to 100 ppm. For soil treatment of the rice fields therewith, its use in a daily amount of 10 to 1000 liters per 1000 m$^2$ with intervals of several days is advisable.

By the application of the 22R,23R-homobrassinolide (I), various useful crop plants including rice, soybean, azuki bean, mung bean, wheat, tomato, cucumber, raddish, carrot, lettuce, orange, apple, grape, etc. are promoted in their growth so that the cultivation period is shortened with improvement of the yield and quality of the crop plants. No injury is caused to those crop plants. When desired, it may be applied together with other plant growth regulators, fertilizers, herbicides, insecticides, fungicides, etc.

Practical and presently preferred embodiments of this invention are illustratively shown in the following examples.

REFERENCE EXAMPLE 1

Preparation of 2α,3α-dihydroxy-24S-ethyl-5α-cholest-22-en-6-one (IV):

Crystals of the compound (III) (6.0 g) were dissolved in acetone (300 ml), and a solution of osmium tetroxdie (300 mg) in t-butanol was added thereto. To the resultant mixture, N-methylmorpholine-N-oxide (6.0 g) was added, and water (10 ml) was added thereto. The resulting mixture was stirred in argon stream for 10 hours. The precipitated crystals were collected by filtration. The filtrate was concentrated, a sodium hydrogen sulfite solution was added thereto to reduce osmium tetroxide, and chloroform was added to the resultant mixture. After addition of celite and activated carbon, the resulting mixture was filtered. The filrate was washed with dilute hydrochloric acid, dried over potassium carbonate and concentrated. The residue was crystallized from a mixture of ether and acetone to give additional crystals. The crystals were combined together and recrystallized from ethanol to give needles (6.35 g). Yield, 97.7%. M.P., 235°–238° C. (decomp.).

$[\alpha]_D^{21}-9.2°$ (c=1.071, CHCl$_3$).

$\nu_{max}$ (nujol) cm$^{-1}$: ~3360 (m), 1715 (s), 1700 (sh), 1330 (w), 1310 (w), 1290 (w), 1265 (w), 1240 (w), 1210 (w), 1165 (w), 1150 (w), 1120 (w), 1105 (w), 1080 (m), 1055 (m), 1040 (m), 1015 (w), 990 (w), 970 (m), 940 (w), 930 (w), 875 (w), 725 (w).

Elementary analysis. Calcd. for C$_{29}$H$_{48}$O$_3$: C, 78.32%; H, 10.88%. Found: C, 77.81%; H, 10.92%.

EXAMPLE 1

Preparation of 2α,3α-diacetoxy-24S-ethyl-5α-cholest-22-en-6-one (IVa):

The compound (IV) as obtained in Reference Example 1 (4.068 g) was dissolved in dry pyridine (50 ml), acetic anhydride (15 ml) and N,N-dimethylaminopyridine (0.1 g) were added thereto, and the resultant mixture was allowed to stand at room temperature overnight. The reaction mixture was poured into ice-dilute hydrochloric acid and extracted with ether. The ether extract was washed with water, sodium hydrogen carbonate solution and sodium chloride solution in order and dried over magnesium sulfate, followed by concentration to give crystals of the compound (IVa). Recrystallization from a mixture of ethyl acetate and petroleum ether gave needles (4.2 g). Yield, 88%. M.P. 187°–188° C.

$[\alpha]_D^{21}-11.6°$ (c=1.088, CHCl$_3$).

$\nu_{max}$ (nujol) cm$^{-1}$: 1745 (s), 1710 (s), 1925 (w), 1255 (s), 1230 (s), 1210 (m), 1190 (w), 1170 (w), 1145 (w), 1105 (w), 1090 (w), 1075 (w), 1035 (m), 1010 (m), 990 (w), 960 (m), 950 (w), 930 (w), 910 (w), 900 (w), 880 (w), 720 (w).

PMR (60 MHz, CDCl$_3$)δ: ~0.6–~1.1 [18H, 0.70 (3H, s), 0.84 (3H, s)], 1.98 (3H, s), 2.08 (3H, s), 4.95 (1H, m), 5.08 (1H, m), 5.38 (1H, m).

Elementary analysis. Calcd. for C$_{33}$H$_{52}$O$_5$: C, 74.96%; H, 9.91%. Found: C, 74.80%; H, 10.04%.

EXAMPLE 2

Preparation of 2R,3S-diacetoxy-24S-ethyl-22,23-oxido-5α-cholestan-6-one (Va):

To a solution of 2R,3S-diacetoxy-24S-ethyl-5α-cholest-22E-en-6-one (IVa) (2313 mg; 4.38 mmol) in methylene chloride (100 ml) while stirring on an ice bath, m-chloroperbenzoic acid (1889 mg; 10.95 mmol) was added. After 30 minutes, the ice bath was removed, and stirring was conducted at room temperature for 5 hours. The reaction mixture was washed with 1N sodium hydroxide solution (100 ml) and water (100 ml) in order, dried over anhydrous sodium sulfate and concentrated under reduced pressure by the aid of a rotary evaporator to obtain a colorless syrup, which was recrystallized from 99% ethanol to give colorless needles (1289 mg). The mother liquor was likewise treated to give additional crystals (949 mg). The crystals were combined together and recrystallized from 99% ethanol to give colorless needles. M.P., 156°–159° C.

$[\alpha]_D^{24}$ −9.16° (c=0.982, CHCl$_3$).

$\nu_{max}$ (nujol) cm$^{-1}$: 1750 (s), 1740 (sh), 1705, 1460 (m), 1440 (sh), 1380 (sh), 1370 (m), 1250 (s), 1230 (m), 1170 (w), 1150 (w), 1120 (w), 1090 (w), 1040 (m), 1025 (sh), 990 (w), 955 (w), 930 (w), 900 (m), 870 (w).

PMR (60 MHz, CDCl$_3$)δ: 0.66 (s, 3H), 0.75–2.85 (m), 1.95 (s, 3H), 2.04 (s, 3H), 2.5 (m, 2H), 4.9 (m, 1H), 5.3 (m, 1H).

CMR (25.0 MHz, CDCl$_3$)δ: 210.2, 170.1, 169.8, 69.1, 68.1.

Elementary analysis. Calcd. for C$_{33}$H$_{52}$O$_6$: C, 72.75%; H, 9.62%. Found: C, 72.77%; H, 9.65%.

EXAMPLE 3

Preparation of 2R,3S,22R,23R-tetraacetoxy-24S-ethyl-5α-cholestan-6-one (VIa):

To 2R,3S-diacetoxy-24S-ethyl-22,23-oxido-5α-cholestan-6-one (Va) (1013 mg; 0.002 mol), 30% hydrobromic acid-acetic acid (4 ml) was added, and stirring was continued at room temperature for 3 hours. The reaction mixture was admixed with water (40 ml) and neutralized with sodium carbonate. The resultant mixture was extracted 3 times with ether, and the extracts were combined together, dried over anhydrous magnesium sulfate and concentrated under reduced pressure by the aid of a rotary evaporator to give a gummy substance (1.3 g).

To the thus obtained gummy substance (1.3 g), glacial acetic acid (40 ml) and water (10 ml) were added, and the resultant mixture was stirred at 90° to 100° C. for 15.5 hours. The reaction mixture was poured into cold sodium bicarbonate solution and extracted with ethyl acetate 3 times. The extracts were combined together, washed with sodium bicarbonate solution 3 times and brine once in order, dried over anhydrous sodium sulfate and concentrated under reduced pressure by the aid of a rotary evaporator. The resultant gummy residue was dissolved in dry pyridine (20 ml), acetic anhydride (20 ml) and 4-N,N-dimethylaminopyridine (50 mg) were added thereto, and stirring was continued at room temperature for 20 hours. The resultant mixture was poured into dilute hydrochloric acid and extracted with ether 2 times. The extracts were combined together, washed with dilute hydrochloric acid 2 times, water once, sodium bicarbonate solution 5 times and brine once in order, dried over anhydrous magnesium sulfate and concentrated under reduced pressure by the aid of a rotary evaporator to give a gummy substance (1.3 g), which was subjected to column chromatography with silica gel (manufactured by Merck; Art. 7734, 70–230 mesh) (78 g) and eluted with 15% ethyl acetate-hexane. Triacetoxybromoketone (218 mg; 17.6%), 2R,3S,22S,23S-tetraacetoxy-24S-ethyl-5α-cholestan-6-one (325 mg; 27.0%) and 2R,3S,22R,23R-tetraacetoxy-24S-ethyl-5α-cholestan-6-one (514 mg; 42.7%) were obtained in this order. Crystallization was unsuccessful.

$[\alpha]_D^{23}$ +3.60° (c=0.639, CHCl$_3$).

$\nu_{max}$ (nujol) cm$^{-1}$: 1740 (s), 1710 (s), 1460 (m), 1370 (ml), 1240 (s), 1220 (s), 1170 (w), 1150 (w), 1105 (w), 1070 (w), 1040 (m), 1020 (m), 985 (w), 978 (w), 945 (w), 900 (w), 880 (w), 855 (w).

PMR (100 MHz, CCl$_4$)δ: 0.71 (s, 3H), 0.76–2.8 (m), 1.92 (s, 6H), 1.98 (s, 3H), 2.02 (s, 3H), 4.7–5.0 (m, 1H), 5.0–5.4 (m, 3H).

2R,3S,22S,23S-Tetraacetoxy-24S-ethyl-5α-cholestan-6-one:

$[\alpha]_D^{23}$ −14.83° (c=0.705, CHCl$_3$).

PMR (100 MHz, CCl$_4$)δ: 0.68 (s, 3H), 0.8–2.8 (m), 1.96 (s, 3H), 2.04 (s, 6H), 2.08 (s, 3H), 4.8–5.1 (m, 2H).

EXAMPLE 4

Preparation of 2R,3S,22R,23R-tetraacetoxy-24S-ethyl-B-homo-7-oxa-5α-cholestan-6-one (Ia):

To a solution of 24S-ethyl-2R,3S,22R,23R-tetraacetoxy-5α-cholestan-6-one (VIa) (323 mg; 0.5 mmol) in dry methylene chloride (15 ml), finely pulverized disodium hydrogen phosphate (1443 mg) was added, followed by stirring. Separately, trifluoroacetic anhydride (1.781 ml) was added to a suspension of 90% hydrogen peroxide (0.273 ml) in dry methylene chloride (2.7 ml) while cooling with ice, followed by stirring. The thus prepared peracid solution was dropwise added to the previously prepared ketone solution while cooling on an ice bath. After removal of the ice bath, the resultant mixture was stirred at room temperature for 30 minutes and then refluxed for 1 hour. After cooling, ice water was added to the reaction mixture. The methylene chloride layer was separated, and the aqueous layer was extracted with methylene chloride. The methylene chloride layer and the methylene chloride extract were combined together, washed with sodium bicarbonate solution, dried over anhydrous magnesium sulfate and concentrated under reduced pressure by the aid of a rotary evaporator to give a gummy substance (362 mg). This substance was subjected to column chromatography with silica gel (manufactured by Merck, Art. 7734; 70–230 mesh; 21 g). The column was eluted with 20 to 30% ethyl acetate-hexane. The obtained colorless syrup (260 mg) was recrystallized from 99% ethanol to give colorless crystals (240 mg). Further recrystallization from 99% ethanol gave plates. M.P., 137°–139° C.

$[\alpha]_D^{24}$ +36.40° (c=0.662, CHCl$_3$).

$\nu_{max}$ (nujol) cm$^{-1}$: 1740 (s), 1720 (sh), 1400 (m), 1370 (m), 1330 (w), 1305 (w), 1248 (s), 1223 (s), 1182 (w), 1170 (w), 1135 (w), 1120 (sh), 1075 (w), 1060 (sh), 1050 (m), 1020 (m), 995 (sh), 980 (w), 942 (w), 715 (w).

PMR (100 MHz, CCl$_4$)δ: 0.76 (s, 3H), 0.8–2.6 (m), 1.91 (s, 3H), 1.98 (s, 3H), 1.95 (s, 3H), 2.04 (s, 3H), 2.93 (m, 1H), 4.02 (m, 2H), 2.6–3.0 (m, 1H), 3.0–3.4 (m, 3H).

Elementary analysis. Calcd. for C$_{37}$H$_5$O$_{10}$: C, 67.04%; H, 8.82%. Found: C, 66.59%, H, 8.73%.

EXAMPLE 5

2R,3S,22R,23R-Tetrahydroxy-24S-ethyl-B-homo-7-oxa-5α-cholestan-6-one (homobrassinolide) (I: R=H):

To a solution of 2R,3S,22R,23R-tetraacetoxy-24S-ethyl-B-homo-7-oxa-5α-cholestan-6-one (Ia) (232 mg) in methanol (20 ml), a solution of sodium hydroxide (480 mg) in water (1.2 ml) was added, and the resultant mixture was stirred while heating with reflux for 3 hours. Stirring was then continued at room temperature for 40 hours. To the reaction mixture, tetrahydrofuran (20 ml) was added, and the resultant mixture on an ice bath was acidified with 6N hydrochloric acid (6 ml) and stirred at room temperature for 4 hours. After evaporation of tetrahydrofuran and methanol under reduced pressure by the aid of a rotary evaporator, the residue was neutralized with sodium hydrogen carbonate and extracted twice with chloroform. The extracts were combined together, dried over anhydrous sodium sulfate and concentrated under reduced pressure by the aid of a rotary evaporator to give colorless crystals (180 mg). Recrystallization from methanol gave colorless fine needles (97 mg). The mother liquor was further concentrated and recrystallized from methanol to give additional fine needle crystals (9 mg). Total yield, 106 mg (61.3%). M.P., 249°–251° C.

$[\alpha]_D^{24}$ +42.88° (c=0.681, CHCl$_3$—CH$_3$OH 9:1).

$\nu_{max}$ (nujol) cm$^{-1}$: 3450 (s), 1730 (s), 1720 (sh), 1695 (s), 1460 (s), 1403 (m), 1377 (s), 1330 (m), 1318 (m), 1290 (w), 1285 (m), 1255 (w), 1220 (w), 1180 (m), 1160 (w), 1140 (w), 1120 (m), 1102 (w), 1060 (s), 1020 (s), 980 (m), 930 (w), 915 (w), 875 (w), 860 (w), 790 (w), 782 (w), 735 (w), 710 (w), 700 (w), 660 (w).

PMR (400.5 MHz, C$_5$D$_5$N)$\delta$: 0.73 (s, 3H), 1.05 (s, 3H), 1.07 (d, J=6.8 Hz, 3H), 1.10 (t, J=7.6 Hz, 3H), 1.15 (d, J=6.8 Hz, 3H), 1.21 (d, J=6.8 Hz, 3H), 1.25–2.27 (m), 2.31 (d, J=4.4 and 14.6 Hz, 1H), 2.51 (ddd, J=2.0, 12.2 and 14.6 Hz, 1H), 3.61 (dd, J=4.4 and 12.2 Hz, 1H), 3.97 (d, J=8.8 Hz, 1H), 4.00–4.14 (m, 4H), 4.43 (br, s, 1H).

CMR (25.0 MHz, CDCl$_3$—CD$_3$OD, 4:1)$\delta$: 178.2, 74.6, 72.8, 71.1, 68.2, 68.2, 58.5, 52.9, 42.9, 41.4, 40.1, 39.6, 38.6, 37.6, 31.7, 29.5, 27.8, 25.1, 22.6, 21.4, 19.7, 19.5, 19.3, 15.6, 13.9, 12.1, 11.9.

Elementary analysis. Calcd. for C$_{28}$H$_{50}$O$_6$: C, 70.41%; H, 10.19%. Found: C, 70.23%; H, 10.20%.

Test 1 (Lamina joint test)

According to the lamina joint test ("Shokubutsu no Kagaku Chosetsu (Chemical Regulation of Plant)", 5, 67–72 (1970)), the plant growth promoting activity of the 22R,23R-homobrassinolide (I: R=H) was examined in comparison with that of known 22S,23S-homobrassinolide.

Namely, the seeds of rice (Kinnampu) were immersed in water at 30° C. under the dark condition for 2 days and sowed in 1% agar media. Cultivation was carried out under a dark condition at 30° C. for 7 days. The seedlings at the growth stage having the tip of the 3rd leaf projected over the leaf sheath of the 2nd leaf were chosen, and the leaf sheath of the 2nd leaf was cut in 2 cm long to obtain test pieces. The resulting test pieces were placed on distilled water under a dark condition at 30° C. for 24 hours. The test pieces giving an angle of 35° between the leaf blade and the leaf sheath (i.e. the inclination angle) under irradiation with red light were collected, and every 6 pieces of them were placed in dishes having each a test solution (10 ml). The dishes were placed at 30° C. under a dark condition for 48 hours. Then, the inclination angle of the leaf blade was measured by the use of a graduator. The results are shown in Table 1.

TABLE 1

| Test Compound | Concentration | Angle of inclination | % |
|---|---|---|---|
| 22R,23R—Homo- | 3 × 10$^{-7}$ M | 138.3 | 190.4 |
| brassinolide | 10$^{-6}$ | 142.0 | 195.4 |
|  | 3 × 10$^{-6}$ | 155.8 | 214.4 |
|  | 10$^{-5}$ | 163.0 | 224.3 |
| (For comparison) | 3 × 10$^{-7}$ M | 127.8 | 175.9 |
| 22S,23S—Homo- | 10$^{-6}$ | 138.5 | 190.6 |
| brassinolide | 3 × 10$^{-6}$ | 146.3 | 201.4 |
|  | 10$^{-5}$ | 147.3 | 202.7 |
| Untreated | 0 | 72.7 | 100 |

From the above results, it is understood that the inclination angle in case of treatment with 22R,23R-homobrassinolide is always greater than that in case of treatment with 22S,23S-homobrassinolide, and the potency of the former is several times that of the latter in lamina joint test.

Test 2 (Azuki bean elongation test)

According to the azuki bean elongation test, the plant physiological activity of 22R,23R-homobrassinolide in the presence of indoleacetic acid (IAA) was compared with that of 22S,23S-homobrassinolide in the presence of IAA.

Seeds of azuki bean soaked in water overnight were sowed into vermiculite and cultivated in an artificial weather room (daily length of 12 hours with 7000 lux at 26° C.). After 6 days, the epicotyl was cut at the distance of 5 mm from the top towards the lower portion to make a piece of 10 mm long. Every 8 pieces were place in a vial admitting phosphate buffer (pH, 6.2; containing 2% sucrose) (4 ml) and a test solution (4 ml). After 48 hours under the same condition as that for growth, the length was measured, and the results are shown in Table 2.

TABLE 2

| Treated | Elongation length (mm) | (%) | Treated | Elongation length (mm) | (%) |
|---|---|---|---|---|---|
| IAA 10$^{-5}$ M + 22R,23R—Homo- brassinolide |  |  | IAA |  |  |
| 10$^{-4}$ M | 10.76 | 414 | 10$^{-4}$ M | 6.40 | 246 |
| 3 × 10$^{-5}$ | 11.27 | 433 | 3 × 10$^{-5}$ | 5.95 | 229 |
| 10$^{-5}$ | 9.30 | 358 | 10$^{-5}$ | 5.15 | 198 |
| 3 × 10$^{-6}$ | 8.65 | 333 | 3 × 10$^{-6}$ | 3.90 | 150 |
| 10$^{-6}$ | 8.05 | 310 | 10$^{-6}$ | 3.50 | 135 |
| 3 × 10$^{-7}$ | 6.45 | 248 | 3 × 10$^{-7}$ | 2.78 | 107 |
| (For comparison) IAA 10$^{-5}$ M + 22S,23S—Homo- brassinolide |  |  | Untreated |  |  |
| 10$^{-4}$ M | 8.85 | 340 |  | 2.60 | 100 |
| 3 × 10$^{-5}$ | 9.10 | 350 |  |  |  |
| 10$^{-5}$ | 8.83 | 340 |  |  |  |
| 3 × 10$^{-6}$ | 8.45 | 325 |  |  |  |
| 10$^{-6}$ | 6.40 | 246 |  |  |  |
| 3 × 10$^{-7}$ | 6.20 | 238 |  |  |  |

In comparison with the sole use of IAA, the combined use of IAA with homobrassinolide produced a remarkable promotion effect on elongation of the piece of azuki bean. The promotion effect of 22R,23R-homobrassinolide was much superior to that of 22S,23S-homobrassinolide.

Test 3 (Test for promotion of growth of azuki bean and rapeseed)

Seeds of azuki bean and rapeseed were sowed in vermiculite. Immediately after the development of the cotyledon or the primary leaf, the seedlings were immersed in a test solution at the root portion for 24 hours and then planted in soil. After cultivation for 20 days, the height and fresh weight of the plants on the ground were measured. For the test, five seedlings were used in each plot, and the results are shown in Table 3 with the average of the five seedlings.

TABLE 3

|  | Treated (ppm) | Height (cm) | Fresh weight (g) |
|---|---|---|---|
| Azuki bean | 22R,23R—Homo- brassinolide |  |  |
|  | 30 | 20.9 | 2.26 |
|  | 10 | 20.3 | 1.98 |
|  | 3 | 19.4 | 1.83 |

TABLE 3-continued

| | Treated (ppm) | Height (cm) | Fresh weight (g) |
|---|---|---|---|
| | (For comparison) 22S,23S—Homobrassinolide | | |
| | 30 | 20.5 | 1.95 |
| | 10 | 18.3 | 1.82 |
| | 3 | 17.7 | 1.75 |
| | Untreated | 16.9 | 1.42 |
| Brassica napus L. | 22R,23R—Homobrassinolide | | |
| | 30 | 12.0 | 1.68 |
| | 10 | 10.4 | 1.62 |
| | 3 | 10.1 | 1.53 |
| | (For comparison) 22S,23S—Homobrassinolide | | |
| | 30 | 10.2 | 1.59 |
| | 10 | 9.7 | 1.52 |
| | 3 | 9.5 | 1.41 |
| | Untreated | 9.2 | 1.31 |

The height and fresh weight of azuki bean and rapeseed in the treated plot with 22R,23R-homobrassinolide were much superior to those in the untreated plot. The elongation promotion effect of 22R,23R-homobrassinolide was several times that of 22S,23S-homobrassinolide.

Test 4 (Test for promotion of fruiting of tomato)

Tomato seedlings (Fukuju No. 2; 55 days after sowing) were planted in 1/5000 are Wagner's pots and cultivated in a glass room. When the first flower opened after 10 days, the flower was treated with homobrassinolide. Likewise, the treatment of the 2nd flower and the 3rd flower was carried out. Using 5 pots for each treatment, the determination of the number of fruiting was made on the 40th day from the first flower treatment. The results are shown in Table 4.

TABLE 4

| | Treated (ppm) | Number of fruits per seedling | | | |
|---|---|---|---|---|---|
| | | 1st | 2nd | 3rd | Total |
| 22R,23R—Homobrassinolide | 30 | 4.0 | 4.4 | 4.4 | 12.8 |
| | 10 | 3.8 | 4.2 | 4.4 | 12.4 |
| | 3 | 3.8 | 4.2 | 4.2 | 12.2 |
| (For comparison) 22S,23S—Homobrassinolide | 30 | 3.6 | 4.0 | 4.2 | 11.8 |
| | 10 | 3.2 | 3.4 | 3.6 | 10.2 |
| | 3 | 2.2 | 2.8 | 3.0 | 8.0 |
| Untreated | — | 2.2 | 2.0 | 1.4 | 5.6 |

As understood from the above, 22R,23R-homobrassinolide showed a significant promoting effect of fruiting of tomato at a concentration of 3 to 30 ppm. The promoting effect of 22S,23S-homobrassinolide appears at a concentration of 3 to 10 ppm, which is inferior to that of 22R,23-homobrassinolide.

What is claimed is:

1. A compound of the formula:

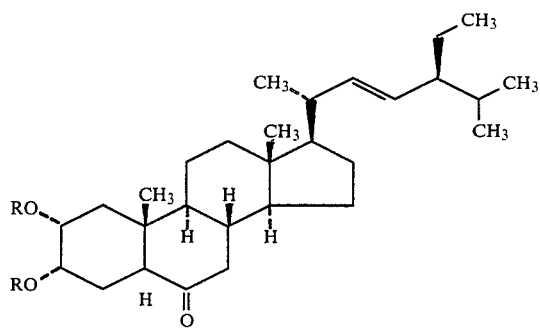

wherein R is an acyl group.

2. A compound of the formula:

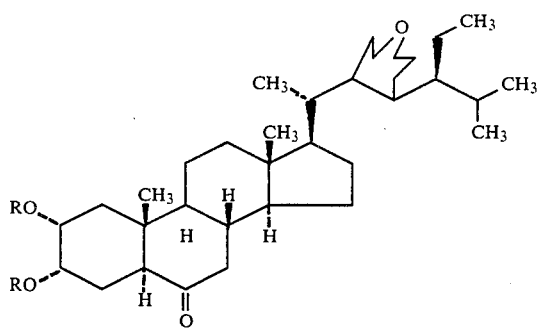

wherein R is a hydrogen atom or an acyl group.

3. A compound of the formula:

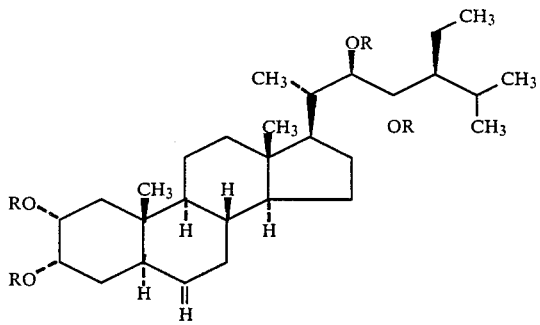

wherein R is a hydrogen atom or an acyl group.

* * * * *